United States Patent
LeBoeuf et al.

(10) Patent No.: US 8,251,903 B2
(45) Date of Patent: Aug. 28, 2012

(54) NONINVASIVE PHYSIOLOGICAL ANALYSIS USING EXCITATION-SENSOR MODULES AND RELATED DEVICES AND METHODS

(75) Inventors: Steven Francis LeBoeuf, Raleigh, NC (US); Jesse Berkley Tucker, Knightdale, NC (US); Michael Edward Aumer, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 975 days.

(21) Appl. No.: 12/256,793

(22) Filed: Oct. 23, 2008

(65) Prior Publication Data
US 2009/0112071 A1 Apr. 30, 2009

Related U.S. Application Data

(60) Provisional application No. 61/000,181, filed on Oct. 25, 2007.

(51) Int. Cl.
*A61B 5/00* (2006.01)
(52) U.S. Cl. .................................................. 600/309
(58) Field of Classification Search .................. 600/309, 600/310, 323, 324
See application file for complete search history.

(56) References Cited

U.S. PATENT DOCUMENTS

| | | | |
|---|---|---|---|
| 5,482,036 A * | 1/1996 | Diab et al. | 600/364 |
| 7,336,982 B2 * | 2/2008 | Yoo et al. | 600/323 |
| 7,486,988 B2 * | 2/2009 | Goodall et al. | 600/546 |
| 7,583,994 B2 * | 9/2009 | Scholz | 600/547 |
| 7,756,559 B2 * | 7/2010 | Abreu | 600/318 |
| 8,050,728 B2 * | 11/2011 | Al-Ali et al. | 600/310 |
| 8,130,105 B2 * | 3/2012 | Al-Ali et al. | 340/573.1 |
| 2005/0058456 A1 * | 3/2005 | Yoo | 398/140 |
| 2006/0211922 A1 * | 9/2006 | Al-Ali et al. | 600/310 |
| 2006/0224059 A1 * | 10/2006 | Swedlow et al. | 600/323 |
| 2009/0030350 A1 | 1/2009 | Yang et al. | |
| 2009/0112071 A1 * | 4/2009 | LeBoeuf et al. | 600/301 |

OTHER PUBLICATIONS

Fitrainer "The Only Trainer You Need"; http://itami.com; Downloaded Feb. 26, 2010; © 2008 FiTriainer™; 2 pages.

* cited by examiner

*Primary Examiner* — Jeffrey G Hoekstra
(74) *Attorney, Agent, or Firm* — Myers Bigel Sibley & Sajovec, P.A.

(57) ABSTRACT

Methods and apparatus for qualifying and quantifying excitation-dependent physiological information extracted from wearable sensors in the midst of interference from unwanted sources are provided. An organism is interrogated with at least one excitation energy, energy response signals from two or more distinct physiological regions are sensed, and these signals are processed to generate an extracted signal. The extracted signal is compared with a physiological model to qualify and/or quantify a physiological property. Additionally, important physiological information can be qualified and quantified by comparing the excitation wavelength-dependent response, measured via wearable sensors, with a physiological model.

42 Claims, 7 Drawing Sheets

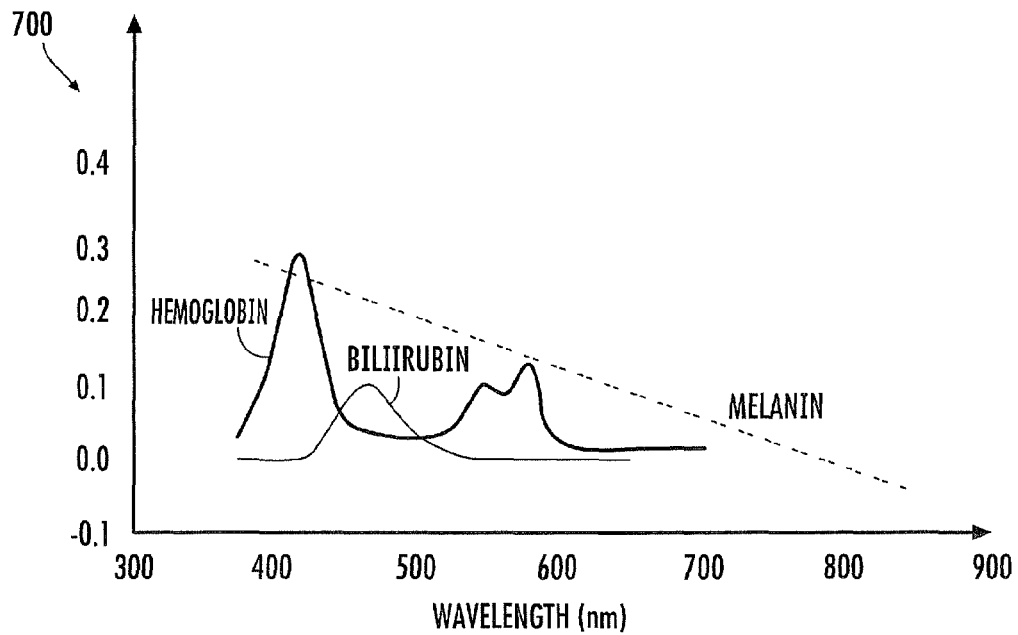
FIG. 7
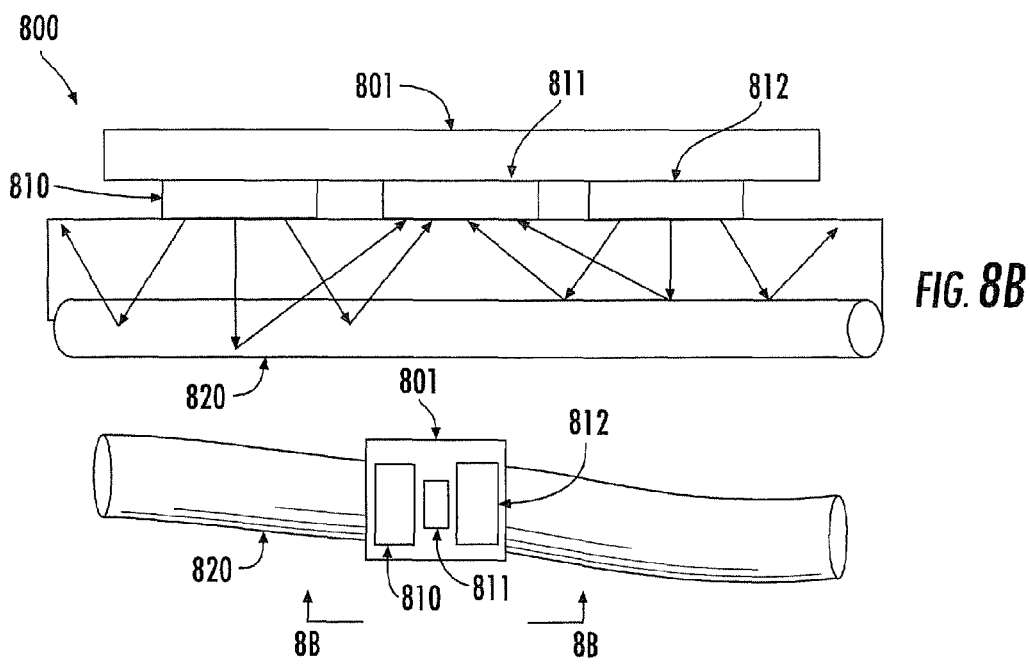
FIG. 8B
FIG. 8A

US 8,251,903 B2

NONINVASIVE PHYSIOLOGICAL ANALYSIS USING EXCITATION-SENSOR MODULES AND RELATED DEVICES AND METHODS

RELATED APPLICATION

This application claims the benefit of and priority to U.S. Provisional Patent Application No. 61/000,181, filed Oct. 25, 2007, the disclosure of which is incorporated herein by reference as if set forth in its entirety.

FIELD OF THE INVENTION

The present invention relates generally to health and, more particularly, to health monitoring.

BACKGROUND OF THE INVENTION

Noninvasive qualification and quantification of physiological properties via wearable sensors may be executed by exciting a physiological region with energy and monitoring the response to that energy with one or more sensors. In wearable pulse oximetry, for example, optical energy from one or more light-emitting diodes (LEDs) excites a region of the body rich with blood vessels (such as a finger tip), and a photodiode senses scattered optical energy relating to blood flow through these blood vessels. Physiological information extracted via such wearable sensor devices may be confounded by a variety of unavoidable factors. Firstly, the extraction of important physiological information may be obscured by unwanted motion artifacts. These motion artifacts may generate false signals that distort physiological information extracted from the wearable sensors. Secondly, the physiological information of interest may be overpowered by unwanted information from neighboring physiological features. For example, pulse oximetry data regarding blood oxygen levels in a blood vessel may be distorted by optical scatter from the skin or blood vessels themselves. Other factors may also confound the physiological information of interest.

SUMMARY

In view of the above discussion, methods and apparatus for qualifying and quantifying excitation-dependent physiological information extracted from wearable sensors in the midst of interference from unwanted sources are provided. According to some embodiments of the present invention, an organism is interrogated with at least one excitation energy, energy response signals from two or more distinct physiological regions are sensed, and these signals are processed to generate an extracted signal. The extracted signal is compared with a physiological model to qualify and/or quantify a physiological property. Additionally, important physiological information can be qualified and quantified by comparing the excitation wavelength-dependent response, measured via wearable sensors, with a physiological model.

According to some embodiments of the present invention, a method of monitoring at least one physiological property (e.g., properties associated with the skin, blood, and/or blood vessels, etc.) of an organism includes directing energy at a target region of the organism; detecting an energy response signal from the target region and an energy response signal from a region adjacent to the target region; processing the detected signals to produce an extracted energy response signal; and comparing the extracted energy response signal with a physiological model to assess a physiological condition of the organism. Energy directed at a target region may include electromagnetic radiation, mechanical energy, acoustical energy, electrical energy, and/or thermal energy.

Processing the detected signals to produce an extracted energy response signal may include subtracting the energy response signal from the region adjacent to the target region from the energy response signal from the target region. In some embodiments, the energy response signal from the target region and the energy response signal from a region adjacent to the target region may be differentially amplified prior to processing. In some embodiments, the extracted energy response signal may be amplified prior to comparing the extracted signal with a physiological model. The extracted energy response signal may be transmitted (e.g., wirelessly, etc.) to a remote device, such as a computing device, communication device, entertainment device, etc.

According to some embodiments of the present invention, directing energy at a target region of the organism includes directing electromagnetic radiation via one or more optical emitters, such as laser diodes (LDs), light-emitting diodes (LEDs), organic light-emitting diodes (OLEDs), etc. In some embodiments, one or more arrays of optical emitters may be utilized to direct energy at a target region. Monolithic and partially monolithic arrays may be utilized. In some embodiments, optical emitters may be configured to direct electromagnetic radiation at different wavelengths, and the detectors may be configured to detect electromagnetic radiation at different wavelengths.

According to some embodiments of the present invention, detecting an energy response signal from the target region and an energy response signal from a region adjacent to the target region includes detecting via one or more detectors, such as acoustic detectors, auscultatory detectors, motion detectors, optical detectors, thermal detectors, piezoelectric detectors, etc. In some embodiments, one or more arrays of detectors can be utilized.

According to some embodiments of the present invention, an apparatus that monitors at least one physiological property of an organism includes at least one energy emitter configured to direct energy at a target region of the organism; at least one detector configured to detect an energy response signal from the target region and an energy response signal from a region adjacent to the target region; and a processor. The processor is configured to process the detected signals to produce an extracted energy response signal, and to compare the extracted energy response signal with a physiological model to assess a physiological condition (e.g., skin properties, blood flow properties, blood pressure, blood vessel properties, etc.) of the organism. The processor is configured to subtract the energy response signal from the region adjacent to the target region from the energy response signal from the target region to produce an extracted energy response signal. In some embodiments, the processor differentially amplifies the energy response signal from the target region and the energy response signal from a region adjacent to the target region prior to producing the extracted energy response signal. In some embodiments, the processor amplifies the extracted energy response signal prior to comparing the extracted energy response signal with a physiological model to assess a physiological condition of the organism.

Energy emitters that direct electromagnetic radiation, mechanical energy, acoustical energy, electrical energy, and/or thermal energy may be utilized. In some embodiments, the at least one energy emitter comprises one or more optical emitters, such as LDs, LEDs, OLEDs, etc. In some embodiments, at least one array of optical emitters are utilized to direct energy at a target region. Monolithic and partially monolithic arrays may be utilized. In some embodiments, optical emitters may be configured to direct electromagnetic radiation at different wavelengths, and the detectors may be configured to detect electromagnetic radiation at different wavelengths.

Detectors utilized to detect an energy response signal from the target region and an energy response signal from a region adjacent to the target region may include auscultatory detectors, motion detectors, optical detectors, thermal detectors, piezoelectric detectors, etc. In some embodiments, one or more arrays of detectors can be utilized. In some embodiments, one or more detectors are utilized to detect an energy response signal from the target region and one or more other detectors are utilized to detect an energy response signal from a region adjacent to the target region. For example, at least one array of detectors may be utilized to detect an energy response signal from the target region and at least one array of detectors may be utilized to detect an energy response signal from a region adjacent to the target region.

Apparatus according to some embodiments of the present invention may include a transmitter in communication with the processor that is configured to transmit (e.g., wirelessly, etc.) the extracted energy response signal to a remote computing device, communication device, and/or entertainment device.

According to other embodiments of the present invention, wearable apparatus for monitoring at least one physiological property of an organism are provided. For example, a wearable apparatus includes a housing configured to be worn by the organism; at least one energy emitter attached to the housing that is configured to direct energy at a target region of the organism; at least one detector attached to the housing that is configured to detect an energy response signal from the target region and an energy response signal from a region adjacent to the target region; and a processor attached to the housing. The processor is in communication with the at least one detector and is configured to process detected signals to produce an extracted energy response signal, and to compare the extracted energy response signal with a physiological model to assess a physiological condition of the organism. In some embodiments, the wearable apparatus is an earpiece that is configured to be attached to an ear of the organism.

According to other embodiments of the present invention, an apparatus that monitors at least one physiological property of an organism includes a processor, and one or more optical emitters configured to direct electromagnetic radiation at a target region of the organism. The optical emitters are configured to be electrically biased by the processor so as to detect an energy response signal from the target region and an energy response signal from a region adjacent to the target region. The processor is configured to process the detected signals to produce an extracted energy response signal, and to compare the extracted energy response signal with a physiological model to assess a physiological condition of the organism.

BRIEF DESCRIPTION OF THE DRAWINGS

FIG. 7 is a graph that illustrates the spectral reflectance response of melanin, bilirubin, and hemoglobin.

FIG. 8A is a top plan view of a device for exciting at least one region with multiple wavelengths of electromagnetic radiation and sensing the response related to each wavelength for comparison with a physiological model, according to some embodiments of the present invention.

FIG. 8B is side elevation view of the device of FIG. 8A, taken along lines 8B-8B.

DETAILED DESCRIPTION

Figure 1:
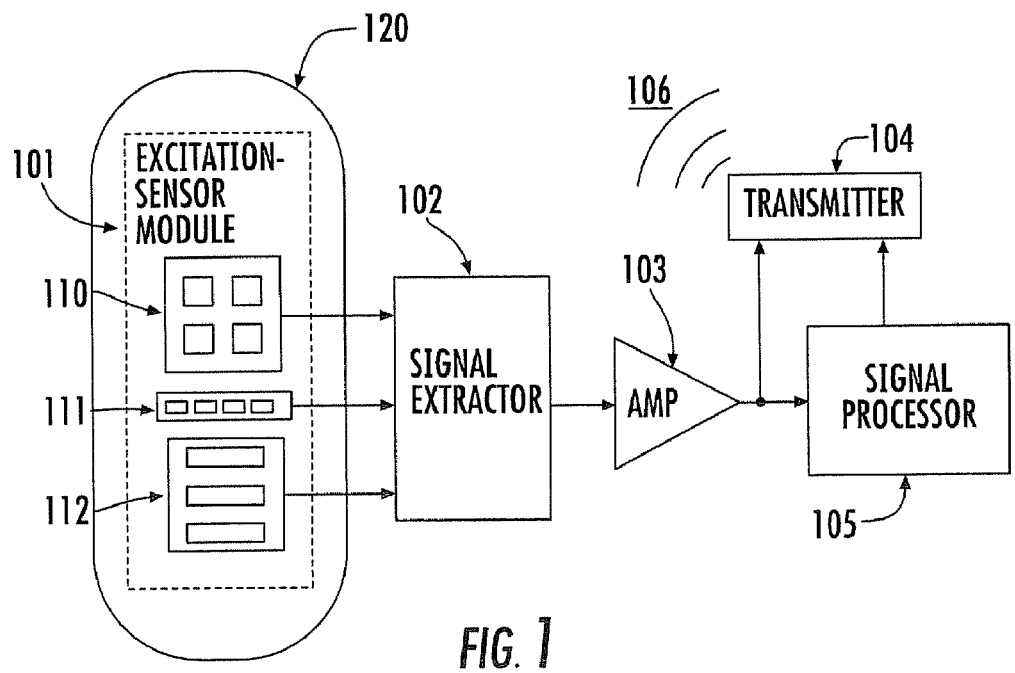
FIG. 1 is a block diagram of a device for noninvasively monitoring a physical property of an organism, according to some embodiments of the present invention.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a creature (e.g., humans, animals, etc.). In embodiments of the present invention, the term "physiological" is intended to be used broadly, covering both physical and psychological matter and energy of or from the body of an organism. However, in some cases, the term "psychological" is called-out separately to emphasize aspects of physiology that are more closely tied to conscious or subconscious brain activity rather than the activity of other organs, tissues, or cells.

The term "body" refers to the body of a person (or animal) that may utilize an earpiece module according to embodiments of the present invention. Monitoring apparatus, according to embodiments of the present invention may be worn by humans and animals.

Referring to FIG. 1, methods and apparatus for qualifying and quantifying one or more physiological properties of an organism, according to some embodiments of the present invention, are illustrated. An extracted signal indicative of the physiological energy response from two or more distinct regions of an organism is generated following the excitation of at least one region via one or more forms of excitation energy. In the illustrated embodiment, an excitation-sensor module 101 is configured to generate and direct excitation energy towards at least one surface 120 of an organism and to sense the energy response from at least two distinct regions of the surface 120. The signal from the excitation-source module may be passed to a signal extractor 102 for processing and/or subtracting the signals to generate at least one extracted signal more closely related to a physiological property of interest. This extracted signal may then be sent to a transmitter 104 for wirelessly transmitting the desired information 106 to another device or network and/or to a signal processor 105 for processing the extracted signal, comparing the processed extracted signal with at least one physiological model, and sending a physiological assessment to the transmitter 104.

The excitation-sensor module 101 may include of one or more excitation source(s) 110, 112, having similar or different excitation elements and/or excitation configurations, as well as one more sensor element(s) 111 having similar or different sensor elements and/or sensor configurations. These is elements (110, 112, and 111) are positioned in contact with, or near to, a surface 120 of an organism. The excitation source(s) 110, 112 can generate energy such as, but not limited to, electromagnetic radiation, mechanical energy, acoustical energy, electrical energy, and/or thermal energy, etc. The sensors 111 can detect one or more of these types of energy.

In some embodiments, an excitation source is a solid-state source, such as a light-emitting diode (LED), laser diode (LD), lamp, radio or microwave transmitter, etc. In some embodiments, a sensor is an acoustic/auscultatory sensor, motion sensor, optical sensor, thermal sensor, etc.

In some embodiments, the excitation sources and sensors are integrated into a wearable device. This wearable device can be configured to process information from the sensors and send processed information telemetrically to another device or network. This other device may be a portable device such as a mobile phone, portable computer, portable entertainment device, embedded computer, or the like. The wearable device may also include at least one communication module for communicating information to the organism and/or entertaining the organism.

Figure 2:
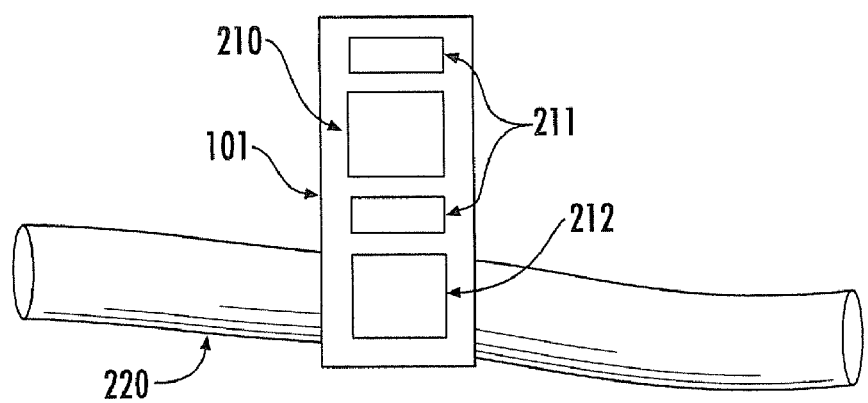
FIG. 2 illustrates the excitation-sensor module of FIG. 1 aligned over a physiological region of interest.

FIG. 2 illustrates an excitation-sensor module 101 positioned noninvasively over the surface 120 (i.e., the skin) of an organism such that an optical emitter 212 is positioned over an area largely covering or completely covering a blood vessel and an optical emitter 210 is positioned over an area near, but not covering, the blood vessel. Optical detectors 211 are arranged to detect scattered excitation light from two separate regions and generate at least two separate electrical signals. Signals related to light scattered from the region lacking a blood vessel can be subtracted from signals related to light scattered from the region covering a blood vessel (e.g., via an electronic circuit). These signals can be subtracted in raw analog form through analog mixers, and these signals can also be digitized first and subtracted in digital form. Regardless, the extracted signal contains "cleaner" information about scattered light coming from the blood vessel itself as compared to light scattered by the blood vessel and neighboring skin tissue. Similarly, as the excitation-sensor module 101 is physically one unit, the effects of motion artifacts can also be subtracted because changes in scattered light at each region will typically happen in unison.

The term "blood vessel", as used herein refers to veins, arteries, capillaries, and the like.

The optical emitters 210, 212 and optical detectors 211 can be solid state devices. For example, the optical emitters 210, 212 can include, but are not limited to, a light-emitting diode (LED), a laser diode (LD), a miniature incandescent lamp, a miniature mercury lamp, a light guide delivering light from an outside source (such as the sun or other light source), a multiwavelength source, a microplasma source, an arc source, a combination of these sources, and the like. Special variants of light-emitting diodes, such as resonant-cavity light emitting diodes (RCLEDs), superluminescent LEDs (SLEDs), organic LEDs (OLEDs), and the like can also be utilized. The optical detectors include, but are not limited to, photodiodes (PDs), avalanche photodiodes (APDs), photomultipliers, or other compact optical detectors.

Though only two optical emitters and optical detectors are shown in FIG. 2, it should be understood that multiple optical emitters and optical detectors can be arranged in an array. The greater the number of optical emitters and detectors in an array, the higher resolution of physiological features and properties that can be extracted. For example, the intensity of optical scatter from a blood vessel at multiple points along the surface of skin covering that blood vessel can be used to judge the size of that blood vessel, without having to calibrate a single optical source for each blood vessel. Unfortunately, increasing the number of optical arrays can increase the fabrication costs of an optical module 101. Additionally, it can become difficult to align and package individual optical sources and detectors on a module for quantifying the size of a blood vessel.

One methodology for reducing the cost and complexity of a high-density optical array is to incorporate a monolithic solid state optical array, such as an LED or LD array. A key benefit of such an array is that solid state optical emitters can alternately operate as optical emitters or optical detectors depending on the electrical biasing. Because these devices can be fabricated monolithically down to the limits of state-of-the-art lithography, a highly dense array of individually controlled LED mesas can be fabricated in a single wafer fabrication run. Thus, an array of optical emitters/detectors can be fabricated self-aligned without needing separate packaging techniques. With such a dense array, the optical emitters can be alternately biased forward and reverse to operate as optical emitters and detectors respectively. For example, for neighboring LED mesas, one LED mesa can be forward-biased to generate light whereas a neighboring LED mesa can be reverse-biased to detect light. When the monolithic array is in proximity to the surface of an organism, the number of mesas detecting significant optical scatter related to a blood vessel can then be used gauge the size of that blood vessel. Similarly, the intensity of optical scatter at each mesa can be used to gauge the size of that blood vessel.

Figure 3:
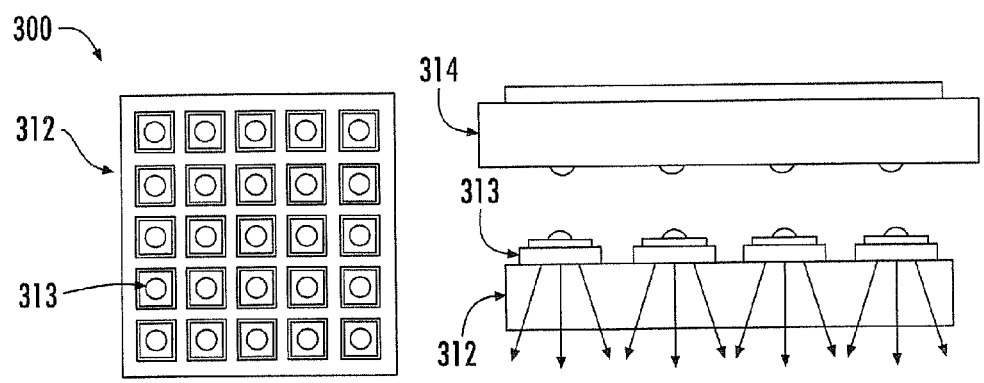
FIG. 3 illustrates an excitation-sensor module comprising a monolithic array of optical emitters operating as emitters or detectors depending on the electrical bias, according to some embodiments of the present invention.
Figure 6:
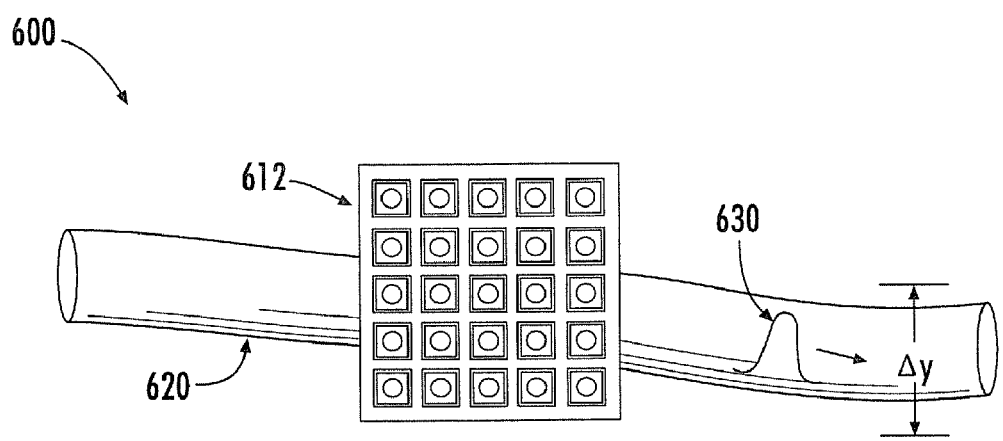
FIG. 6 illustrates an excitation-sensor array, accord to some embodiments of the present invention, being used to qualify and/or quantify physiological properties of a blood vessel and/or blood, such as blood pressure or metabolic status of the blood.

FIG. 3 illustrates an exemplary monolithic optical emitter array 312 containing individually controlled optical emitters 313 which can also be biased as optical detectors. Though a variety of techniques can be used to control the bias through each mesa, one technique is to bond the metal contacts of each individual mesa to a mounting package 314 having metal bumps aligned to the monolithic array 313 and having circuitry for controlling each individual mesa separately. This packaging forms a module 300 with the array. FIG. 6 shows how an excitation-sensor array module 612, such as a monolithic optical emitter array module 300, may be aligned to a blood vessel 620 for gauging the size or shape of the blood vessel, as well as extracting a cleaner signal relating physiological information about the blood vessel 620.

Figure 5A:
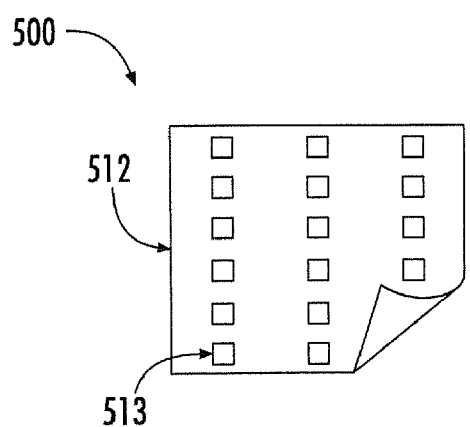
FIGS. 5A-5B illustrate flexible piezoelectric arrays that may be utilized in accordance with embodiments of the present invention.
Figure 5B:
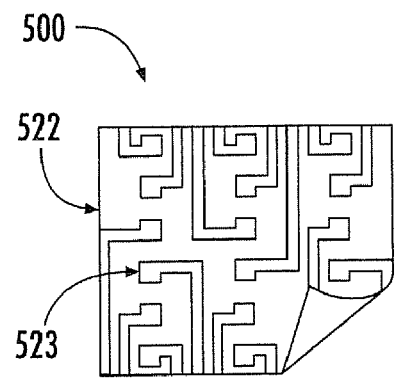

The fabrication of solid-state monolithic optical arrays is well known to those skilled in the art. Solid-state monolithic optical arrays can be semiconductor optical arrays, such as LED or LD arrays, organic LED arrays, such as OLEDs and the like. OLED arrays can offer a benefit of being flexed, as shown in FIGS. 5A-5B, at least partially around a blood vessel. OLEDs can also be dual-based as optical emitters and detectors, but separate optical detectors can also be printed within an array. The print-style manufacturing technique for fabricating organic electronics makes the manufacture of organic/polymer device arrays potentially less costly and tedious than that of traditional LED arrays. Because of the ability to "print" device components for organic electronics, OLED arrays, organic photodetector arrays, and organic piezoelectric arrays can be deposited in the same module and interlaced in the same array. This adds higher-level physiological sensing functionality by increasing the number of physiological-related parameters that can be monitored at the same time.

Piezoelectric arrays can also be employed for noninvasively monitoring the physiological properties of an organism, according to some embodiments of the present invention. This allows mechanical energy from some piezoelectric elements to couple with a region of the organism while other piezoelectric elements measure the response. The processing of this information to generate information on physiological dimensions or physiological properties can be the same as that described for monolithic LED arrays 312.

Figure 4:
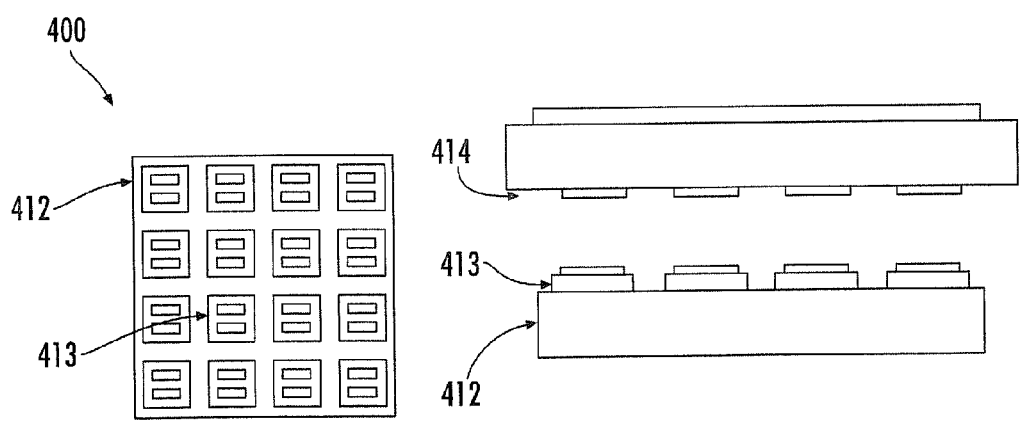
FIG. 4 illustrates an excitation-sensor module comprising an array of piezoelectric sensors operating as both mechanical energy generators as well as mechanical energy sensors depending on the electrical bias, according to some embodiments of the present invention.

Many polar semiconductors contain piezoelectric properties, and thus several types of device arrays on several types of semiconductors can be used as piezoelectric sensors and/or actuators, according to embodiments of the present invention. For example, metal arsenides and metal nitrides, such as aluminum indium gallium arsenide or aluminum indium gallium nitride alloys, and the like, can be used to fabricate piezoelectric arrays. The elements of these arrays can be micro-manufactured or nano-manufactured as cantilevers, membranes, flexible rods, or the like using standard microelectromechanical systems (MEMS) and nanoelectromechanical (NEMS) fabrication techniques. Similarly, simple device structures such as field effect transistors, resistors, and even light-emitting diodes can be operated as piezoelectric sensors. Thus, an LED array can be used as both an optical emitter-detector array or piezoelectric sensing array depending on the biasing of the array. Methods of fabricating piezoelectric arrays are well known to those skilled in the art. The monolithic piezoelectric actuator-sensor array 400 of FIG. 4 can be fabricated as an array 412 of metallic contacts 413 on a semiconductor surface, where the surface may or may not be defined into individual mesas. The packaging module 414 can be employed in the same manner as package 314 of FIG. 3.

As described earlier, flexible organic/polymer arrays can also be employed for physiological monitoring as shown in FIG. 6. The array elements (e.g., 513, FIG. 5A) can come from any number of optical emitting (OLED), optical detecting (OLED or organic photodetector), piezoelectric (such as polarized fluoropolymers), or other sensing elements. A secondary screen-printed (or similar) film 523 (FIG. 5B), which may be deposited on the organic polymer array layer 512 or on a separate layer 522, can be used to electrically access each device element 513. In the case of a polymer piezoelectric array 500, polarized polymers, such as polyvinylidene fluoride (PVDF), can be used as an active piezoelectric element for generating and/or sensing mechanical energy is from an organism. For example, by generating mechanical energy with one filament in the array and detecting the mechanical energy response coming from the organism at other filaments, a physiological map of a feature, such as a blood vessel, can be processed. This can be used to gauge the size of a blood vessel opening and closing in time.

Embodiments of the present invention can be used to assess blood pressure or blood pressure properties in a blood vessel.

For example, the information on the size of a blood vessel, as well as the change in size of a blood vessel during blood flow, can be combined with information regarding the total flow of blood to assess blood pressure. Namely, the size and change of size in a blood vessel can relate the area of a blood vessel, and this can be combined with the volumetric flow rate of blood to gauge or estimate blood pressure.

Referring to FIG. 6, reflective pulse oximetry can be combined with blood vessel size estimation via optical scatter detection, according to some embodiments of the present invention. For example, an optical emitter generating blue light can be used to generate an optical scatter signal more closely related to the size of a blood vessel, shown by Δy in FIG. 6. An optical emitter generating IR light can be used to generate an optical scatter signal more closely related to the blood flow in the blood vessel, shown by 630 in FIG. 6. A third and fourth optical emitter, violet and red respectively, may be located near (but not covering) the blood vessel, for example in an arrangement as that illustrated in FIG. 2. Optical scatter signals from these sources are more closely related to optical scatter from the skin or other tissue. Thus, when these skin-related optical scatter signals are differentially amplified with respect to their blood-vessel-related counterparts, at least two extracted signals can be generated that are more closely related to the size of a blood vessel and the blood flow rate through a blood vessel. These extracted signals can then be digitized, processed, and compared with a physiological model related to blood pressure to qualify and quantify blood pressure in real time.

The aforementioned IR scatter signal more closely related to the blood flow in the blood vessel may also contain some information related to the optical scatter from the expanding blood vessel wall. Thus, differentially amplifying the aforementioned blue scatter signal more closely related to the size of a blood vessel with respect to the aforementioned IR scatter signal can help subtract artifacts associated with expanding blood vessel size from the desired blood flow information. Thus, second order affects can be alleviated, to at least some degree, from the overall assessment of blood pressure.

Embodiments of the present invention can be utilized for qualifying and quantifying a variety of physiological properties in physiological tissue and fluids. For example, the optical scatter signal associated with blood glucose in a blood vessel can be more accurately and/or precisely extracted. In another embodiment, blood hemoglobin components, such as oxyhemoglobin, methemoglobin, carboxyhemoglobin, and the like, can be more accurately and/or precisely extracted. In these embodiments, the optical scatter response associated with the skin is subtracted from the optical scatter response associated with skin+blood metabolites to generate a clean extracted signal more closely related to blood metabolite quality and quantity. In each case, the optical signal associated with scatter from the skin tissue is separated from the optical signal associated with the blood vessel or blood components. This embodiment utilizes multiple emitters, multiple detectors, or both, with each emitter and detector located in a distinct region in the vicinity of a blood vessel—either directly over the blood vessel or near but not covering the blood vessel. If the optical emitters and detectors are located too far apart from the region of interest, it can be difficult to extract the desired physiological-related signal. This is because optical scatter from separate areas can be too dissimilar for successful differential amplification and extraction of a clear physiologically related signal.

In some embodiments of the present invention, the same sensors, sensor configurations, and processing, can be used to extract signals related to the physiological properties of the skin. For example, information related to the size of a blood vessel or flow of blood through a blood vessel can be subtracted from an optical scatter signal reflected from the skin. This will yield cleaner information more closely related to the physiological properties of the skin, such as skin metabolite levels, hydration, elasticity, and the like.

Figure 9:
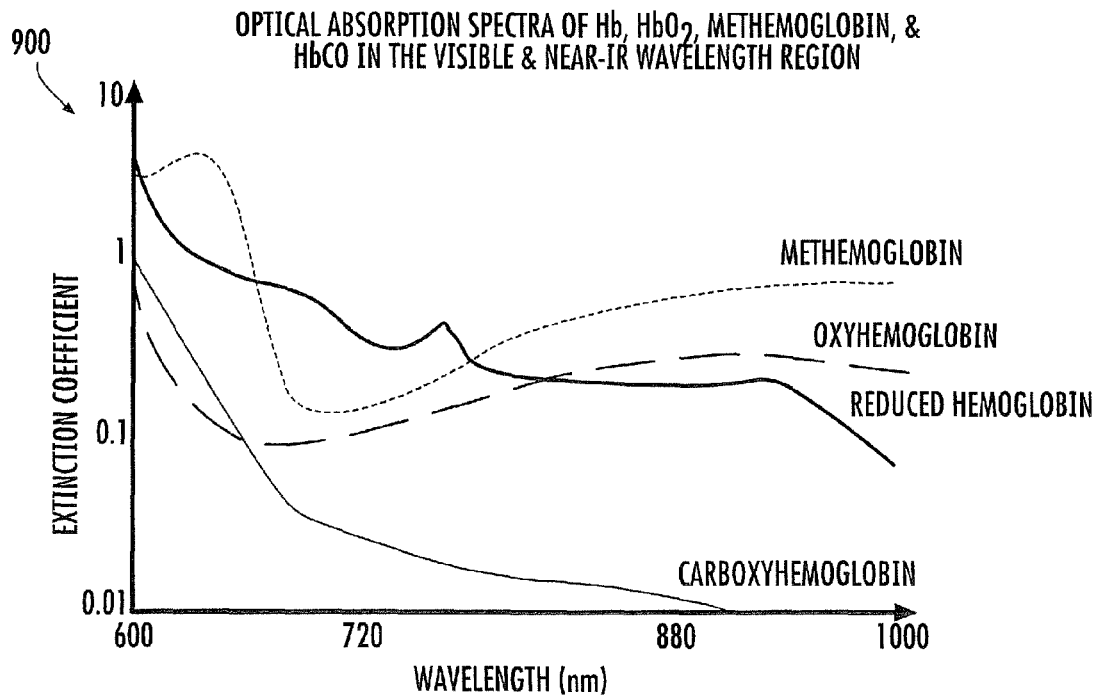
FIG. 9 is a graph that illustrates the spectral extinction coefficient of various forms of hemoglobin.

As described above, the scatter intensity of light for each wavelength of electromagnetic excitation can be used to qualify and/or quantify a particular physiological parameter. For example, in humans, shorter wavelength optical radiation (blue-UV) reflects largely from the skin, whereas longer wavelength radiation (red-IR) can penetrate through blood vessels (FIG. 7). Thus, an approach for qualifying and/or quantifying at least one physiological property of an organism according to some embodiments of the present invention is to generate at least two extracted signals, each indicative of at least one physiological energy response from at least one region of the organism following the electromagnetic excitation of at least one region with at least two wavelengths of electromagnetic excitation. The wavelength-dependent energy response from each region can then be sensed by at least one neighboring sensor and/or sensor array and converted into at least two electrical signals. This energy response can be mechanical, acoustical/auscultatory, electrical, or thermal in origin. The two or more electrical signals can be converted into extracted signals by filtering out each signal with respect to noise, as described earlier. These extracted signals are each indicative of at least one physiological energy response to at least one wavelength of electromagnetic energy. These extracted signals can then be amplified, compared, processed, and compared with at least one physiological model to qualify and/or quantify at least one physiological property of the organism. One specific example of physiological properties that can be extracted, such as blood metabolites, is shown in FIG. 9.

A specific embodiment of noninvasively qualifying and/or quantifying a particular physiological parameter is shown in FIGS. 8A-8B. In this embodiment, the electromagnetic excitation sources, 810, 812, are optical emitters. Optical emitter 810 generates long wavelength radiation and optical emitter 812 generates short wavelength radiation. The optical detector 811 converts the optical scatter from the optical emitters 810, 812 into an electrical signal. The short wavelength optical emitter 812 generates optical radiation which is reflected from the surface of the blood vessel 820, whereas the long wavelength optical emitter 810 generates optical radiation which is at least partially reflected from the blood inside the blood vessel. If the optical emitters 810, 812 are pulsed and synchronized in time with the optical detector 811, at least two separate signals can be extracted for each excitation wavelength. For example, the electrical signal associated with the short wavelength optical energy from the optical source 812 is more closely associated with the size of the blood vessel 820, whereas the electrical signal associated with the long wavelength optical energy from the optical source 810 is more closely associated with the blood flow through the blood vessel. Thus, as described earlier, by comparing these independent signals, an assessment of blood pressure can be estimated.

Embodiments of the present invention described herein can be quite useful when integrated into a wearable device, such as a wearable telemetric device. In some embodiments, a wearable device can communicate telemetrically with a portable computer or portable communication device, such as a cellular phone, personal digital assistant, or the like. Thus, a person wearing the device can view a real-time assessment of personal vital signs through a portable view screen. In some embodiments, this telemetric information can be transmitted through a cellular network and onto the world-wide-web for storage in a database. This stored data can then be accessed through the web. Devices according to embodiments of the present invention can be comprised of compact, low-power solid-state devices, such as LEDs, photodiodes, piezoelectric elements, microphones, NEMS/MEMS devices, or the like. As such, embodiments of the present invention can be integrated into wearable monitors.

Figure 10:
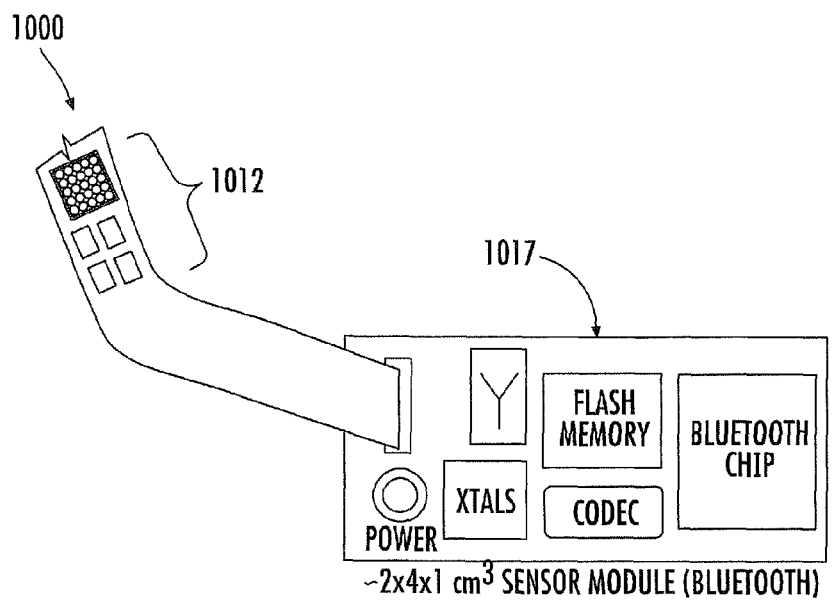
FIG. 10 is a block diagram of a wearable telemetric device, according to some embodiments of the present invention.

FIG. 10 illustrates the use of excitation-sensor modules 1012 in a wearable physiological monitor 1000. The modules 1012 can be integrated into a flexible circuit board or flexible connector, connected to a Bluetooth processing board. Flexible circuit boards are typically fabricated from a polymer with integrated copper electrodes and circuit paths.

Figure 11:
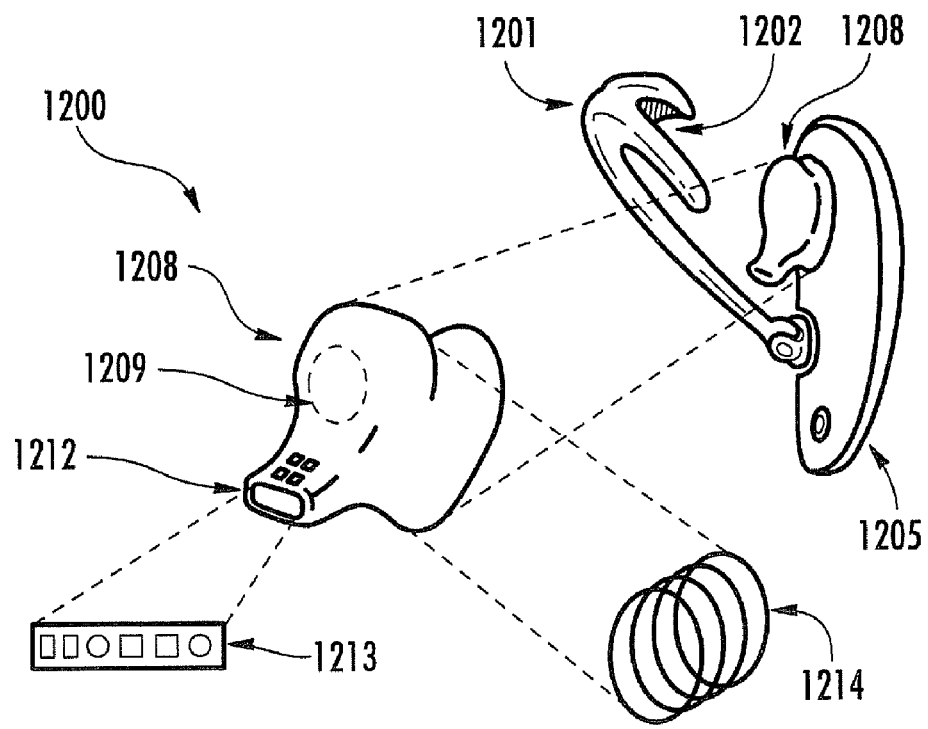
FIG. 11 is an exploded perspective view of a telemetric hands-free audio headset capable of both telemetric personal communications and/or/entertainment and physiological monitoring, that can be utilized to implement various embodiments of the present invention.
Figure 12:
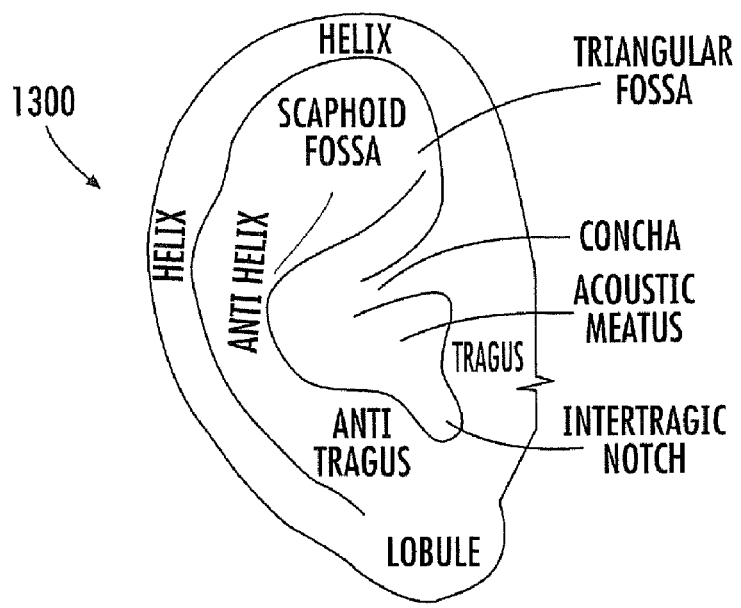
FIG. 12 illustrates the anatomy of the human ear.

In a particular embodiment, the wearable physiological monitor 1000 can be integrated into the main body 1205 of a telemetric earpiece, as shown in FIG. 11. FIG. 11 illustrates details about the location of sensors in certain parts of an earpiece module 1205, according to embodiments of the present invention. The ear support 1201 contains a pinna (helix) cover 1202 that may contain sensors for monitoring physiological and environmental factors. This structure is particularly useful for sensing methodologies which require energy to be transmitted through the thin layers of the pinna (the outer ear). Though any portion of the pinna can be covered and/or contacted, in some embodiments, the pinna cover 1202 overlaps at least a part of the helix or a part of the scapha of an ear (FIG. 12 illustrates a human ear). Likewise, an optical absorption detector, composed of an optical emitter and optical detector, can be integrated into the pinna cover 1202 for monitoring, for example, hydration, dosimetry, skin temperature, inductive galvanometry, conductive galvanometry, and the like.

Galvanometry, the measurement of electrical properties of the skin, can be measured inductively, through contactless electromagnetic induction without contacts, or conductively, with two, three, four, or more conductivity probes. Additionally, a 4-point conductivity probe technique, such as that used for measuring the conductivity of semiconductor wafers, can be applied. A variety of sensors can be integrated into the earpiece fitting 1208. For example, a galvanometric device can be integrated into the surface 1209 of the earpiece fitting where the earpiece fitting touches the skin of the outer ear. A particularly strong pulse response can be monitored with excitation-sensor modules such as those described above mounted in the earpiece fitting region 1209, touching the acoustic meatus (FIG. 12). Additionally, an inductive device, such as an inductive coil 1214, can be integrated along the earpiece fitting body to measure movements of the tympanic membrane inductively. The inductive impedance can also be measured with the inductive coil 1214 or another inductive sensor, and this can be applied towards contactless galvanometry. The inductive coil 1214 can include one or more coils arranged in any orientation, and a core material, such as an iron-containing material, may be used to improve the sensitivity of the response. In some cases, multiple coils may be used to facilitate the canceling of stray electromagnetic interference. Sensors can also be integrated into the end tip 1212 of the earpiece fitting 1208 to measure physiological properties deeper into the ear canal. For example, the modules of FIGS. 2-4 and 5A-5B may be located in, at, or near the end tip region 1212 in a module 1213. The sensors on the module 1213 in this region are carefully arranged so as not to prevent the transmission of sound (from the built-in communication module) and to not be distorted during earpiece placement and removal. The end tip sensor module 1213 can contain several types of sensors for generating multiple types of energy and detecting multiple types of energy, and this module can be integrated into the speaker module (part of the communication module) inside the earpiece fitting 1208 that is used for sound transmission to the user during telemetric conversations. In some embodiments, the speaker module can be used as a microphone to measure auscultatory signals from the body. This may be especially useful for measuring low frequency signals less than 1000 Hz. Employing the speaker as a microphone may require impedance matching to maximize the auscultatory signal extraction. The modules of FIGS. 2-4 and 5A-5B can be located in, at, or near other parts of the earpiece module, such as the earpiece fitting 1208 surface 1209, the ear support 1201, or the earpiece body 1205.

Figure 13:
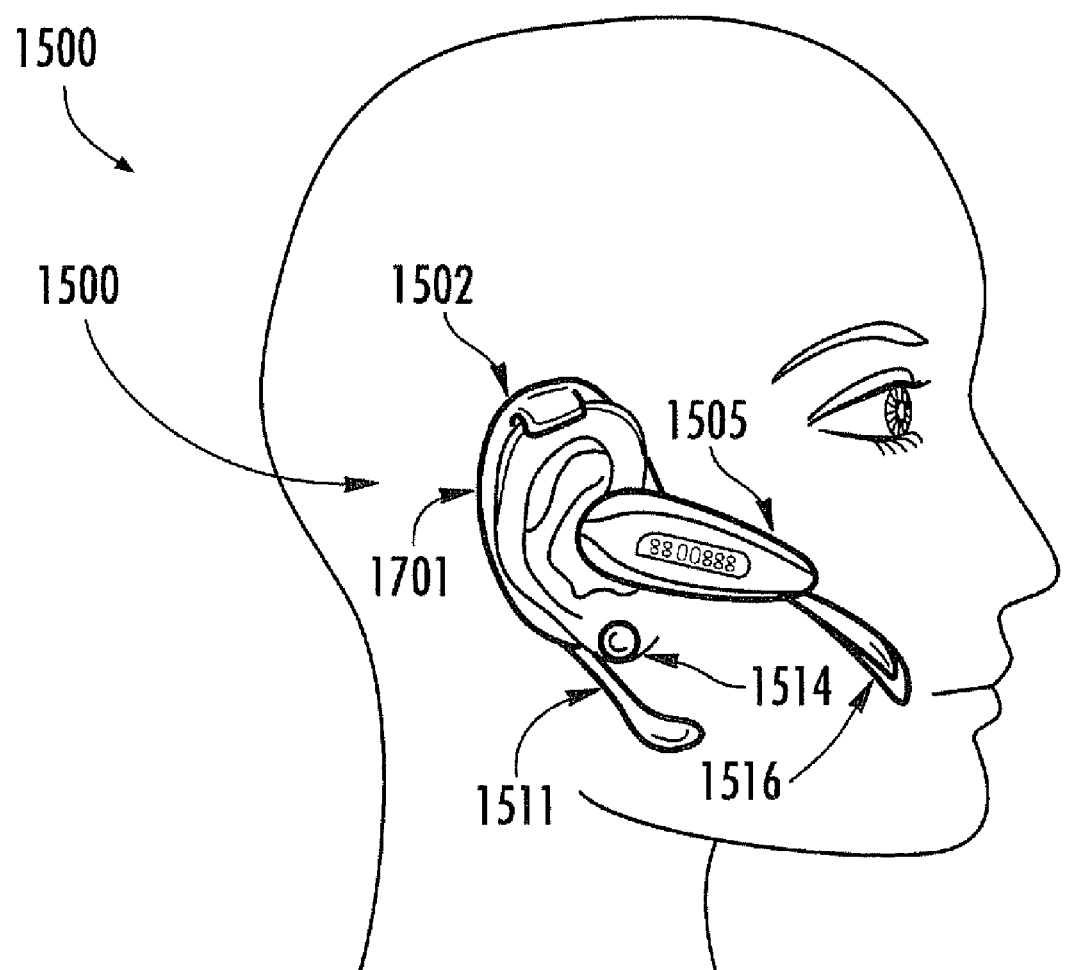
FIG. 13 illustrates the hands-free headset of FIG. 11 being worn by a person.

Another multifunctional earpiece module 1500, according to embodiments of the present invention, is illustrated in FIG. 13. The illustrated earpiece module 1500 includes the embodiments illustrated in FIG. 11, such as a pinna cover 1502, an ear support 1501, a mouthpiece 1516, an earpiece body 1505, and the like. Additionally, the earpiece module 1500 may contain an extension 1511 with sensors for monitoring jaw motion, arterial blood flow near the neck, or other physiological and environmental factors near the jaw and neck region.

The person illustrated in FIG. 15 is also wearing an earring monitor 1514 according to embodiments of the present invention. Because at least one portion of an earring may penetrate the skin, earring monitor 1514 may contain sensors and telemetric circuitries that provide access to various blood analytes through iontophoresis and electrochemical sensing that may not be easily accessible by the other portions of the earpiece module 1500. Additionally, the earring monitor 1514 may provide a good electrical contact for ECG or skin conductivity.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A method of monitoring at least one physiological property of an organism, comprising:
    directing energy at a target region of the organism and at a region adjacent the target region, wherein the target region comprises substantially more blood vessels than the adjacent region;
    detecting an energy response signal from the target region and an energy response signal from the adjacent region, wherein the directing and detecting steps are performed by a device worn by the organism;
    processing the detected signals to produce an extracted energy response signal; and
    comparing the extracted energy response signal with a physiological model to assess a physiological condition of the organism.

2. The method of claim 1, wherein directing energy at the target region and adjacent region comprises directing electromagnetic radiation, mechanical energy, acoustical energy, electrical energy, and/or thermal energy at the target region and adjacent region.

3. The method of claim 1, wherein processing the detected signals to produce an extracted energy response signal comprises subtracting the energy response signal from the region adjacent to the target region from the energy response signal from the target region.

4. The method of claim 1, further comprising differentially amplifying the energy response signal from the target region and the energy response signal from a region adjacent to the target region prior to the processing step.

5. The method of claim 1, further comprising amplifying the extracted energy response signal prior to the comparing step.

6. The method of claim 1, further comprising transmitting the extracted energy response signal to a remote device.

7. The method of claim 6, wherein transmitting the extracted energy response signal to a device comprises wirelessly transmitting the extracted energy response signal.

8. The method of claim 6, wherein the device is selected from the group consisting of computing devices, communication devices, and entertainment devices.

9. The method of claim 1, further comprising transmitting the extracted energy response signal to the organism.

10. The method of claim 1, wherein directing energy at the target region and adjacent region of the organism comprises directing electromagnetic radiation via at least one optical emitter.

11. The method of claim 8, wherein the at least one optical emitter is selected from the group consisting of laser diodes (LDs), light-emitting diodes (LEDs), and organic light-emitting diodes (OLEDs).

12. The method of claim 8, wherein the at least one optical emitter comprises at least one array of optical emitters.

13. The method of claim 1, wherein detecting an energy response signal from the target region and an energy response signal from a region adjacent to the target region comprises detecting via at least one detector selected from the group consisting of acoustic detectors, auscultatory detectors, motion detectors, optical detectors, thermal detectors, and piezoelectric detectors.

14. The method of claim 1, wherein the physiological condition of the organism includes properties of skin, blood, and/or blood vessels of the organism.

15. The method of claim 1, wherein the physiological condition of the organism comprises one or more of the following: blood pressure, volume of blood flow through a blood vessel, and size of at least one blood vessel.

16. The method of claim 1, wherein the target region comprises vascular and non-vascular tissue, and wherein the adjacent region is dominated by non-vascular tissue.

17. The method of claim 1, wherein directing energy at a target region of the organism comprises directing electromagnetic radiation via at least one optical emitter and wherein detecting energy response signals from the target region and region adjacent to the target region comprises electrically biasing at least one optical emitter to operate as an optical detector.

18. The method of claim 12, wherein the at least one array of optical emitters comprises at least one monolithic array of optical emitters.

19. The method of claim 12, wherein the at least one array of optical emitters comprises at least one partially monolithic array of optical emitters.

20. The method of claim 1, wherein directing energy at a target region of the organism comprises directing electromagnetic radiation at different wavelengths.

21. The method of claim 1, wherein detecting an energy response signal from the target region and an energy response signal from a region adjacent to the target region comprises detecting electromagnetic radiation at different wavelengths.

22. The method of claim 21, further comprising measuring blood flow in the organism by detecting electromagnetic radiation at a first wavelength and measuring motion of the organism by detecting electromagnetic radiation at a second wavelength that is shorter than the first wavelength.

23. The method of claim 1, wherein processing the detected signals to produce an extracted signal comprises subtracting a signal associated with motion from a signal associated with a physiological condition of the organism.

24. The method of claim 1, wherein the device is a wearable device that comprises a plurality of emitters and a plurality of detectors.

25. A method of monitoring at least one physiological property of an organism, comprising:
   directing energy at a target region of the organism, wherein the target region has a substantial amount of blood vessels;
   detecting an energy response signal from the target region and an energy response signal from a region adjacent the target region, wherein the adjacent region has a substantially less amount of blood vessels than the target region, wherein the directing and detecting steps are performed by a device worn by the organism;
   processing the detected signals to produce an extracted energy response signal; and
   comparing the extracted energy response signal with a physiological model to assess a physiological condition of the organism.

26. The method of claim 25, wherein directing energy at the target region comprises directing electromagnetic radiation, mechanical energy, acoustical energy, electrical energy, and/or thermal energy at the target region.

27. The method of claim 25, wherein processing the detected signals to produce an extracted energy response signal comprises subtracting the energy response signal from the region adjacent to the target region from the energy response signal from the target region.

28. The method of claim 25, further comprising amplifying the extracted energy response signal prior to the comparing step.

29. The method of claim 25, further comprising transmitting the extracted energy response signal to a remote device.

30. The method of claim 29, wherein transmitting the extracted energy response signal to a device comprises wirelessly transmitting the extracted energy response signal.

31. The method of claim 30, wherein the device is selected from the group consisting of computing devices, communication devices, and entertainment devices.

32. The method of claim 25, further comprising transmitting the extracted energy response signal to the organism.

33. The method of claim 25, wherein directing energy at the target region of the organism comprises directing electromagnetic radiation via at least one optical emitter.

34. The method of claim 33, wherein the at least one optical emitter is selected from the group consisting of laser diodes (LDs), light-emitting diodes (LEDs), and organic light-emitting diodes (OLEDs).

35. The method of claim 33, wherein the at least one optical emitter comprises at least one array of optical emitters.

36. The method of claim 25, wherein detecting an energy response signal from the target region and an energy response signal from a region adjacent to the target region comprises detecting via at least one detector selected from the group consisting of acoustic detectors, auscultatory detectors, motion detectors, optical detectors, thermal detectors, and piezoelectric detectors.

37. The method of claim 25, wherein the physiological condition of the organism includes properties of skin, blood, and/or blood vessels of the organism.

38. The method of claim 25, wherein the physiological condition of the organism comprises one or more of the following: blood pressure, volume of blood flow through a blood vessel, and size of at least one blood vessel.

39. The method of claim 25, wherein the target region comprises vascular and non-vascular tissue, and wherein the adjacent region is dominated by non-vascular tissue.

40. The method of claim 25, wherein directing energy at a target region of the organism comprises directing electromagnetic radiation via at least one optical emitter and wherein detecting energy response signals from the target region and region adjacent to the target region comprises electrically biasing at least one optical emitter to operate as an optical detector.

41. The method of claim 25, wherein processing the detected signals to produce an extracted signal comprises subtracting a signal associated with motion from a signal associated with a physiological condition of the organism.

42. The method of claim 25, wherein the device is a wearable device that comprises a plurality of emitters and a plurality of detectors.

* * * * *